US006942619B2

(12) United States Patent
Toda

(10) Patent No.: US 6,942,619 B2
(45) Date of Patent: Sep. 13, 2005

(54) ULTRASOUND RADIATION DEVICE

(76) Inventor: Kohji Toda, 1-49-18 Futaba, Yokosuka (JP), 239-0814

(*) Notice: Subject to any disclaimer, the term of this patent is extended or adjusted under 35 U.S.C. 154(b) by 596 days.

(21) Appl. No.: 10/153,568

(22) Filed: May 20, 2002

(65) Prior Publication Data

US 2003/0216647 A1 Nov. 20, 2003

(51) Int. Cl.[7] .................................................. A61B 8/14
(52) U.S. Cl. ...................... 600/459; 310/313 B; 73/602
(58) Field of Search ................................ 600/437–472; 73/602, 627, 625, 626, 628, 629, 632, 642, 593; 367/7, 11, 130, 138, 89, 90, 91, 101, 102; 310/313 B, 313 C, 150–155; 128/916

(56) References Cited

U.S. PATENT DOCUMENTS

| | | | | | |
|---|---|---|---|---|---|
| 5,239,516 A | * | 8/1993 | Kimura | ........................ | 367/91 |
| 5,331,247 A | * | 7/1994 | Ikeda et al. | ............. | 310/313 B |
| 5,441,052 A | * | 8/1995 | Miyajima | .................... | 600/455 |
| 6,212,129 B1 | * | 4/2001 | Nussbaumer et al. | .......... | 367/89 |
| 6,564,649 B1 | * | 5/2003 | Toda | ........................ | 73/861.26 |
| 6,640,631 B1 | * | 11/2003 | Toda | ........................... | 73/597 |
| 6,640,636 B1 | * | 11/2003 | Toda | ........................... | 73/651 |
| 6,691,577 B1 | * | 2/2004 | Toda | ........................... | 73/602 |
| 6,755,082 B2 | * | 6/2004 | Toda | ........................... | 73/597 |

* cited by examiner

*Primary Examiner*—Ali Imam

(57) ABSTRACT

An ultrasound radiation device comprises a piezoelectric substrate, an interdigital arrangement of two comb-shaped electrodes formed on an upper end surface of the piezoelectric substrate, a counter electrode formed on a lower end surface of the piezoelectric substrate, an interdigital transducer formed on said upper end surface of said piezoelectric substrate, and an amplifier between one of the two comb-shaped electrodes and the interdigital transducer. If an electric signal is applied between the counter electrode and one of the two comb-shaped electrodes, a longitudinal wave composed of the main lobe and grating lobes is radiated into a material in contact with the counter electrode, as well as a Lamb wave is excited in the piezoelectric substrate. The Lamb wave is detected as a delayed electric signal at the interdigital transducer. The delayed electric signal is amplified by the amplifier, and used as an input electric signal again.

20 Claims, 17 Drawing Sheets

ULTRASOUND RADIATION DEVICE

BACKGROUND OF THE INVENTION

1. Field of the Invention

The present invention relates to a device for radiating an ultrasound into a material by means of using a piezoelectric substrate, an interdigital arrangement of two comb-shaped electrodes formed on an upper end surface of the piezoelectric substrate, a counter electrode formed on a lower end surface of the piezoelectric substrate, an interdigital transducer, and an amplifier.

2. Description of the Prior Art

For the purpose of radiating an ultrasound into a liquid, a thickness mode piezoelectric transducer with parallel plate-like electrodes is usually used. Such a conventional type of transducer has a difficulty in controlling the radiation angle into the liquid, and particularly in radiation toward a slant direction. In addition, the conventional type of transducer has a difficulty in high-frequency operation. On the other hand, an interdigital transducer on the piezoelectric substrate operates at a liquid-solid boundary as a leaky wave transducer for bulk wave radiation into the liquid. The leaky SAW traveling on a sufficiently thick substrate compared with the wavelength has only one mode without velocity dispersion. Thus, conventional transducers such as the thickness mode piezoelectric transducer and the interdigital tansducer for the leaky SAW have the problem of the limited ultrasound-radiation angle.

SUMMARY OF THE INVENTION

An object of the present invention is to provide an ultrasound radiation device making an interdigital arrangement of two comb-shaped electrodes act as a thickness mode transducer.

Another object of the present invention is to provide an ultrasound radiation device capable of controlling the radiation angle into the material.

Another object of the present invention is to provide an ultrasound radiation device operating with a high efficiency.

Another object of the present invention is to provide an ultrasound radiation device capable of low electric power consumption.

Another object of the present invention is to provide an ultrasound radiation device capable of radiating an ultrasound into a cellular tissue.

Another object of the present invention is to provide an ultrasound radiation device capable of radiating an ultrasound into a cellular tissue having an ointment thereon through a skin, so that making the ointment permeate into the cellular tissue.

Another object of the present invention is to provide an ultrasound radiation device excellent in durability and manufacturing.

A still other object of the present invention is to provide an ultrasound radiation device easy in use and having a small size which is very light in weight and has a simple structure.

According to one aspect of the present invention there is provided an ultrasound radiation device comprising a piezoelectric substrate, an interdigital arrangement of two comb-shaped electrodes, a counter electrode, an interdigital transducer, and an amplifier between one of the two comb-shaped electrodes and the interdigital transducer. The interdigital arrangement of the two comb-shaped electrodes is formed on an upper end surface of the piezoelectric substrate. The counter electrode is formed on a lower end surface of the piezoelectric substrate and in contact with a material through the lower end surface of the counter electrode. The interdigital transducer is formed on the upper end surface of the piezoelectric substrate.

If an electric signal is applied between the one of the two comb-shaped electrodes and the counter electrode, a longitudinal wave composed of the main lobe and grating lobes is radiated into the material. At the same time, a Lamb wave is excited in the piezoelectric substrate. The Lamb wave is detected at the interdigital transducer as a delayed electric signal, which is amplified via the amplifier, and supplied to the one of the two comb-shaped electrodes as an input electric signal again.

According to another aspect of the present invention there is provided an ultrasound radiation device, wherein the finger width in the one of the two comb-shaped electrodes is wider than that in the other of the two comb-shaped electrodes.

According to another aspect of the present invention there is provided an ultrasound radiation device, wherein increasing the number of electrode-finger pairs in the interdigital arrangement suppresses the grating lobes under a condition that the total amount of all the finger-areas of the one of the two comb-shaped electrodes is constant.

According to another aspect of the present invention there is provided an ultrasound radiation device, wherein making the ratio of the interdigital periodicity of the interdigital arrangement to the thickness of the piezoelectric substrate smaller than four times the ratio of the longitudinal wave velocity in the material to the longitudinal wave velocity in the piezoelectric substrate suppresses the grating lobes.

According to another aspect of the present invention there is provided a piezoelectric substrate made of a piezoelectric ceramic plate, the polarization axis thereof being parallel to the thickness direction thereof.

According to another aspect of the present invention there is provided an ultrasound radiation device radiating the longitudinal wave into a liquid matter.

According to another aspect of the present invention there is provided an ultrasound radiation device radiating the longitudinal wave into a cellular tissue.

According to another aspect of the present invention there is provided a polymer film, with which the lower end surface of the counter electrode is coated.

According to another aspect of the present invention there is provided a nonpiezoelectric plate formed on said lower end surface of said piezoelectric substrate.

According to another aspect of the present invention there is provided an ultrasound radiation device, which radiates the longitudinal wave into a cellular tissue having an ointment thereon through a skin.

According to another aspect of the present invention there is provided a scanning system composed of groups of switches, which correspond to the electrode-fingers of the one of the two comb-shaped electrodes, respectively. One and the next of the groups have common switches each other except the first switch of the one of the groups and the last switch of the next of the groups. If input electric signals are applied between the one of the two comb-shaped electrodes and the counter electrode via the groups in turn, longitudinal waves are radiated into the material in the form of a scanned ultrasound beam as a whole.

According to another aspect of the present invention there is provided an ultrasound radiation device comprising a piezoelectric substrate, a comb-shaped electrode, a counter electrode, an interdigital transducer, and an amplifier between the comb-shaped electrode and the interdigital transducer. The comb-shaped electrode is formed on the upper end surface of the piezoelectric substrate. The counter electrode is formed on the lower end surface of the piezoelectric substrate and in contact with a material through the lower end surface of the counter electrode. The interdigital transducer is formed on the upper end surface of the piezoelectric substrate.

If an electric signal is applied between the comb-shaped electrode and the counter electrode, a longitudinal wave composed of the main lobe and grating lobes are radiated into the material, At the same time, a Lamb wave is excited in the piezoelectric substrate, The Lamb wave is detected at the interdigital transducer as a delayed electric signal, which is amplified via the amplifier, and supplied to the comb-shaped electrode as an input electric signal again.

According to another aspect of the present invention there is provided an ultrasound radiation device, wherein increasing the number of electrode-fingers in the comb-shaped electrode suppresses the grating lobes under a condition that the total amount of all the finger-areas of the comb-shaped electrode is constant.

According to other aspect of the present invention there is provided an ultrasound radiation device, wherein making the ratio of the interdigital periodicity of the comb-shaped electrode to the thickness of the piezoelectric substrate smaller than four times the ratio of the longitudinal wave velocity in the material to the longitudinal wave velocity in the piezoelectric substrate suppresses the grating lobes.

According to a further aspect of the present invention there is provided a scanning system composed of groups of switches, which correspond to the electrode-fingers of the comb-shaped electrode, respectively. One and the next of the groups have common switches each other except the first switch of the one of the groups and the last switch of the next of the groups. If input electric signals are applied between the comb-shaped electrode and the counter electrode via the groups in turn, longitudinal waves are radiated into the material in the form of a scanned ultrasound beam as a whole.

BRIEF DESCRIPTION OF THE DRAWINGS

Other features and advantages of the invention will be clarified from the following description with reference to the attached drawings.

DETAILED DESCRIPTION OF THE PRESENTLY PREFERRED EXEMPLARY EMBODIMENTS

Figure 1:
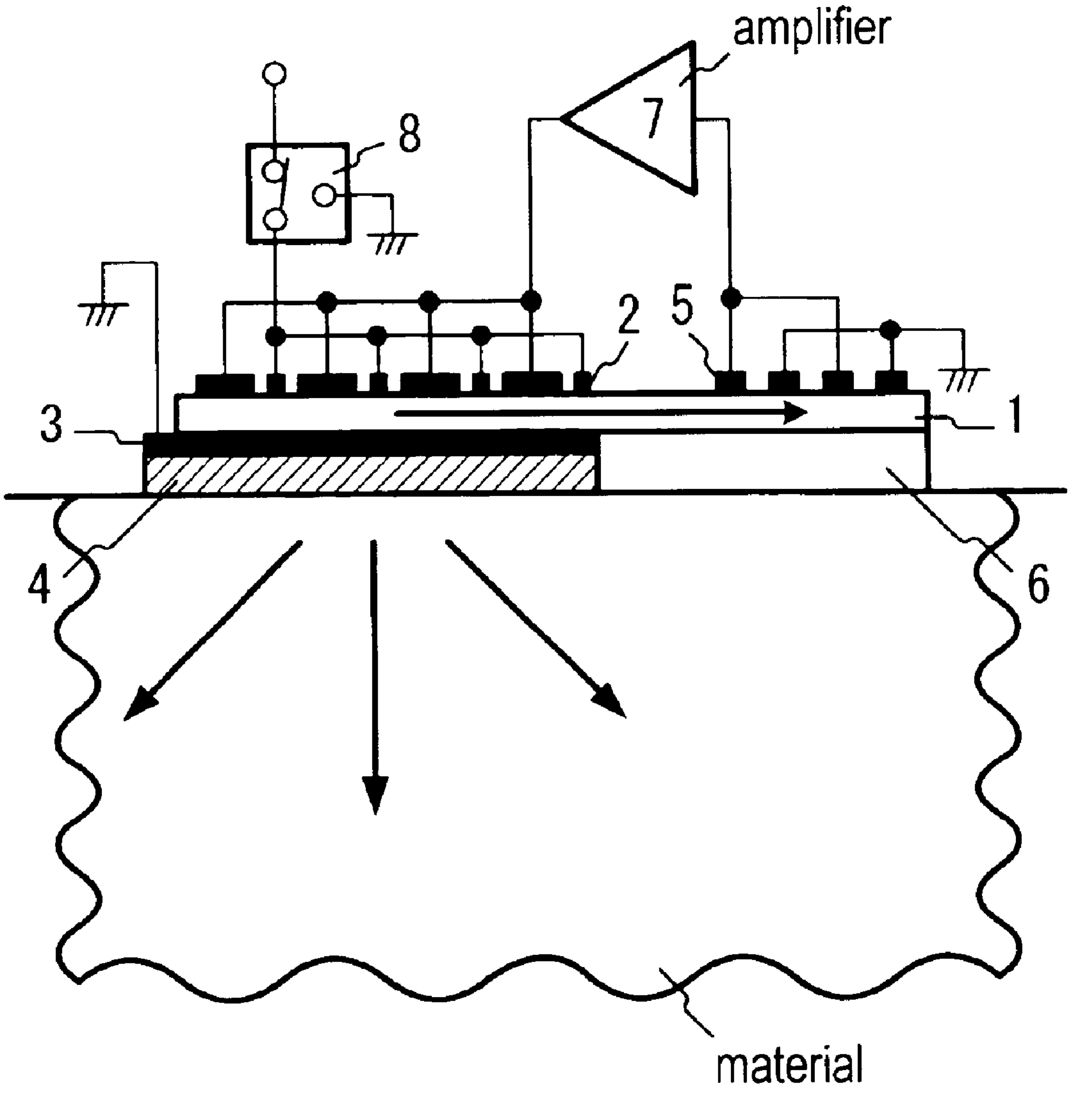
FIG. 1 shows a sectional view of an ultrasound radiation device according to a first embodiment of the present invention.

FIG. 1 shows a sectional view of an ultrasound radiation device according to a first embodiment of the present invention. The ultrasound radiation device comprises piezoelectric substrate 1, interdigital arrangement 2 of two comb-shaped electrodes (2A and 2B), counter electrode 3, silicone rubber 4, interdigital transducer 5, glass plate 6, amplifier 7, and switch 8. Piezoelectric substrate 1 is made of a piezoelectric ceramic plate with a thickness (T) of 500 $\mu$m, and the polarization axis thereof is parallel to the thickness direction thereof. Interdigital arrangement 2 and interdigital transducer 5, made of an aluminum thin film, respectively, are formed on an upper end surface of piezoelectric substrate 1. Interdigital transducer 5 has an interdigital periodicity of 900 $\mu$m. Counter electrode 3, made of an aluminum thin film, is formed on one surface part of a lower end surface of piezoelectric substrate 1. Glass plate 6 is cemented on the other surface part of the lower end surface of piezoelectric substrate 1. The lower end surface of counter electrode 3 is coated with silicone rubber 4. Thus, the ultrasound radiation device in FIG. 1 has a small size, which is very light in weight and has a simple structure. The lower end surface of silicone rubber 4 and that of glass plate 6 are in contact with a material.

Figure 2:
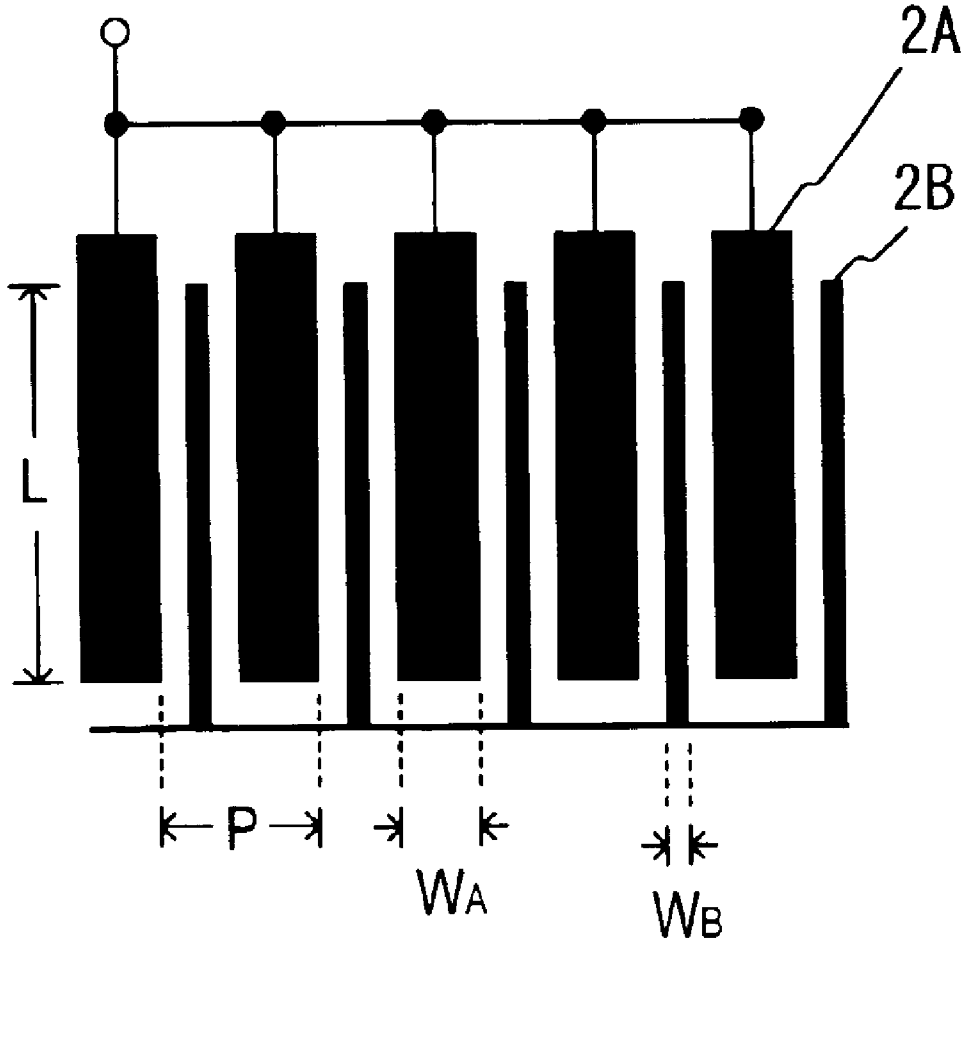
FIG. 2 shows a top plan view of interdigital arrangement 2.

FIG. 2 shows a top plan view of interdigital arrangement 2. Interdigital arrangement 2 has five electrode-finger pairs, a finger-overlap length (L) of 5 mm, and an interdigital periodicity (P) of 900 $\mu$m, which is the same as interdigital transducer 5. Comb-shaped electrode 2A has a finger width ($W_A$) of 180 $\mu$m, and comb-shaped electrode 2B has a finger width ($W_B$) of 48 $\mu$m. Amplifier 7 is connected between comb-shaped electrode 2A and interdigital transducer 5 in FIG. 1. Switch 8 makes a condition that comb-shaped electrode 2B is electrically floated or grounded.

In the ultrasound radiation device in FIG. 1, if an electric signal is applied between counter electrode 3 and comb-shaped electrode 2A, a longitudinal wave composed of the main lobe and grating lobes is radiated into the material through the lower end surface of silicone rubber 4. At the same time, a Lamb wave is excited in piezoelectric substrate 1. The Lamb wave is transmitted to interdigital transducer 5 along the parallel direction with the end surfaces of piezoelectric substrate 1. In this time, the use of glass plate 6 prevents the leakage of the Lamb wave into the material, because of glass plate 6 having a phase velocity larger than that of piezoelectric substrate 1. Thus, the Lamb wave is detected at interdigital transducer 5 as a delayed electric signal, which is amplified via amplifier 7 and supplied to comb-shaped electrode 2A as an input electric signal again. Thus, supplying comb-shaped electrode 2A with the input electric signal via amplifier 7 causes a self-oscillation, and moreover causes the circuit construction simplified.

As mentioned above, the longitudinal wave is radiated into the material. If the material is water, the longitudinal wave velocity in water ($V_W$) is approximately 1,500 m/s, and the longitudinal wave velocity in piezoelectric substrate 1 (V) is 4,500 m/s. Thus, the ratio of the $V_W$ value to the V value, that is 1,500/4,500, is approximately 0.333. On the other hand, the ratio of the interdigital periodicity (P) of interdigital arrangement 2 to the thickness (T) of piezoelectric substrate 1, that is 900/500, is 1.8, which is larger than four times the ratio of the $V_W$ value to the V value. Such a condition of $P/T \geqq 4V_W/V$ makes the longitudinal wave composed of the main lobe and the grating lobes effectively radiated into water. As a result, the condition of $P/T \geqq 4V_W/V$ enables a multidirectional radiation into a material. In addition, the condition that comb-shaped electrode 2B is electrically floated or grounded has influence upon the intensity of the grating lobes. When comb-shaped electrode 2B is electrically grounded, there exist the larger grating lobes.

The longitudinal wave is effectively radiated into, for example, a cellular tissue. In this time, if the cellular tissue has an ointment thereon through a skin, the ointment permeates into the cellular tissue effectively. As a result, the ultrasound radiation device in FIG. 1 behaves like a syringe for injection.

Figure 3:
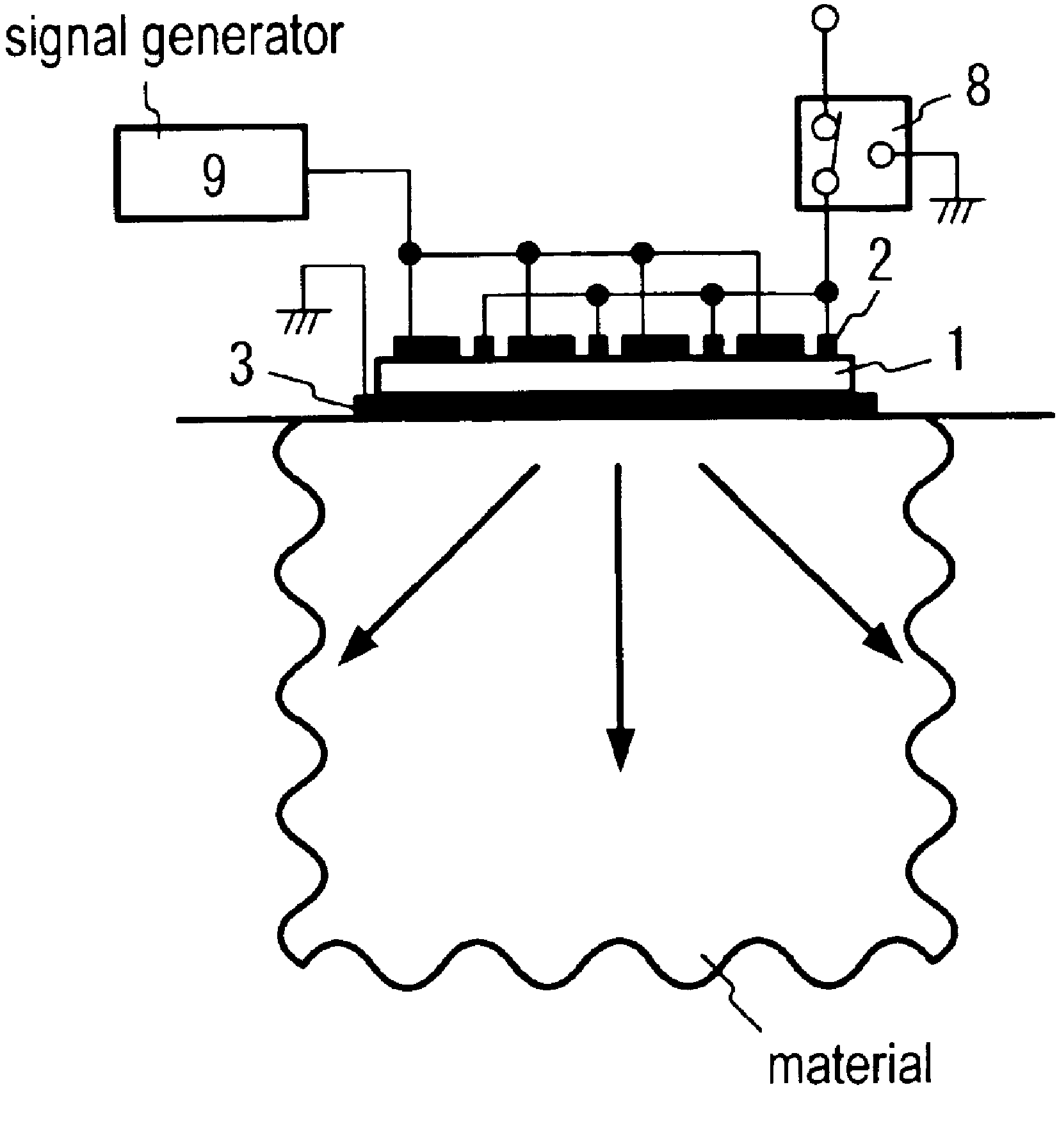
FIG. 3 shows a sectional view of an ultrasound radiation device according to a second embodiment of the present invention.

FIG. 3 shows a sectional view of an ultrasound radiation device according to a second embodiment of the present invention. The ultrasound radiation device comprises piezoelectric substrate 1, interdigital arrangement 2, counter electrode 3, switch 8, and signal generator 9.

In the ultrasound radiation device in FIG. 3, if an electric signal from signal generator 9 is applied between counter electrode 3 and comb-shaped electrode 2A, a longitudinal wave composed of the main lobe and grating lobes is radiated into the material through the lower end surface of counter electrode 3. In this time, the condition that comb-shaped electrode 2B is electrically floated or grounded has influence upon the intensity of the grating lobes. When comb-shaped electrode 2B is electrically floated, there exist smaller grating lobes.

Figure 4:
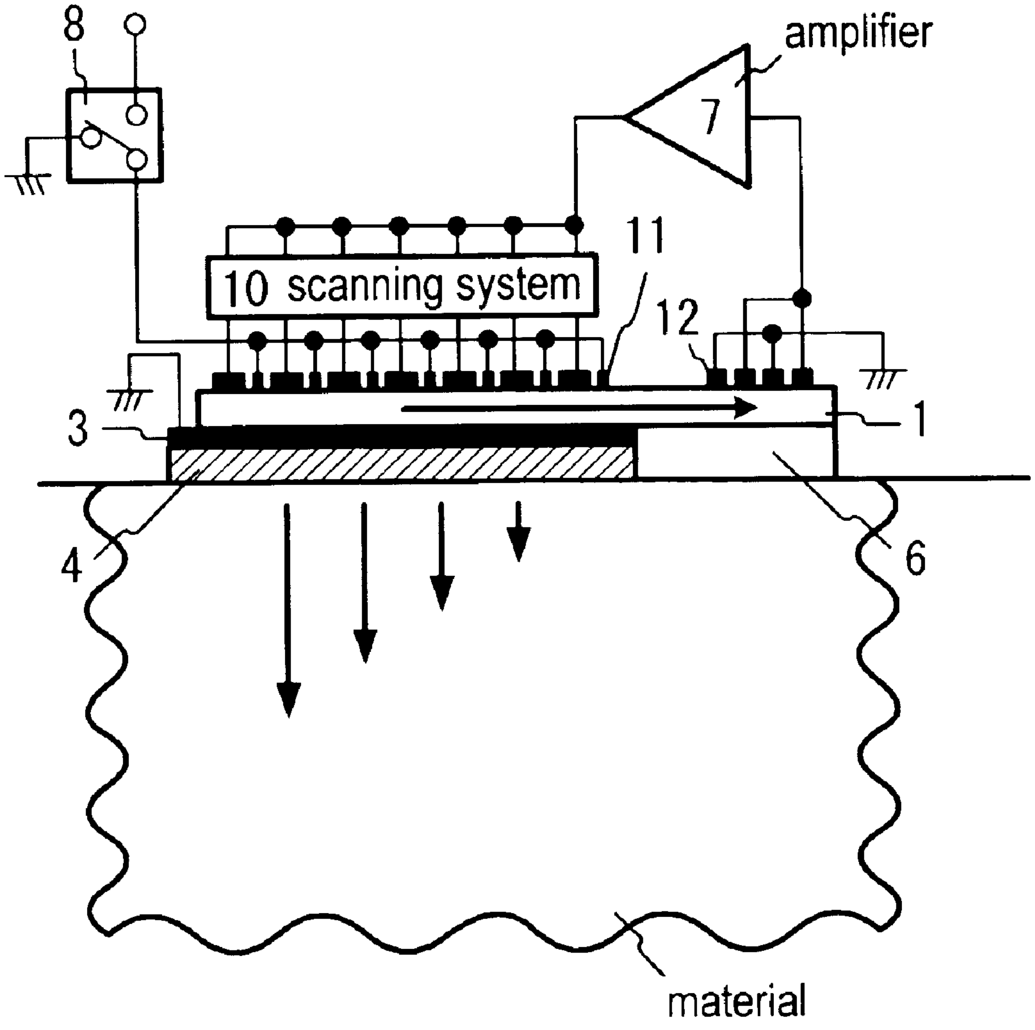
FIG. 4 shows a sectional view of an ultrasound radiation device according to a third embodiment of the present invention.

FIG. 4 shows a sectional view of an ultrasound radiation device according to a third embodiment of the present invention. The ultrasound radiation device comprises piezoelectric substrate 1, counter electrode 3, silicone rubber 4, glass plate 6, amplifier 7, switch 8, scanning system 10, interdigital arrangement 11 of two comb-shaped electrodes (11A and 11B), and interdigital transducer 12 having an interdigital periodicity of 225 μm.

Figure 5:
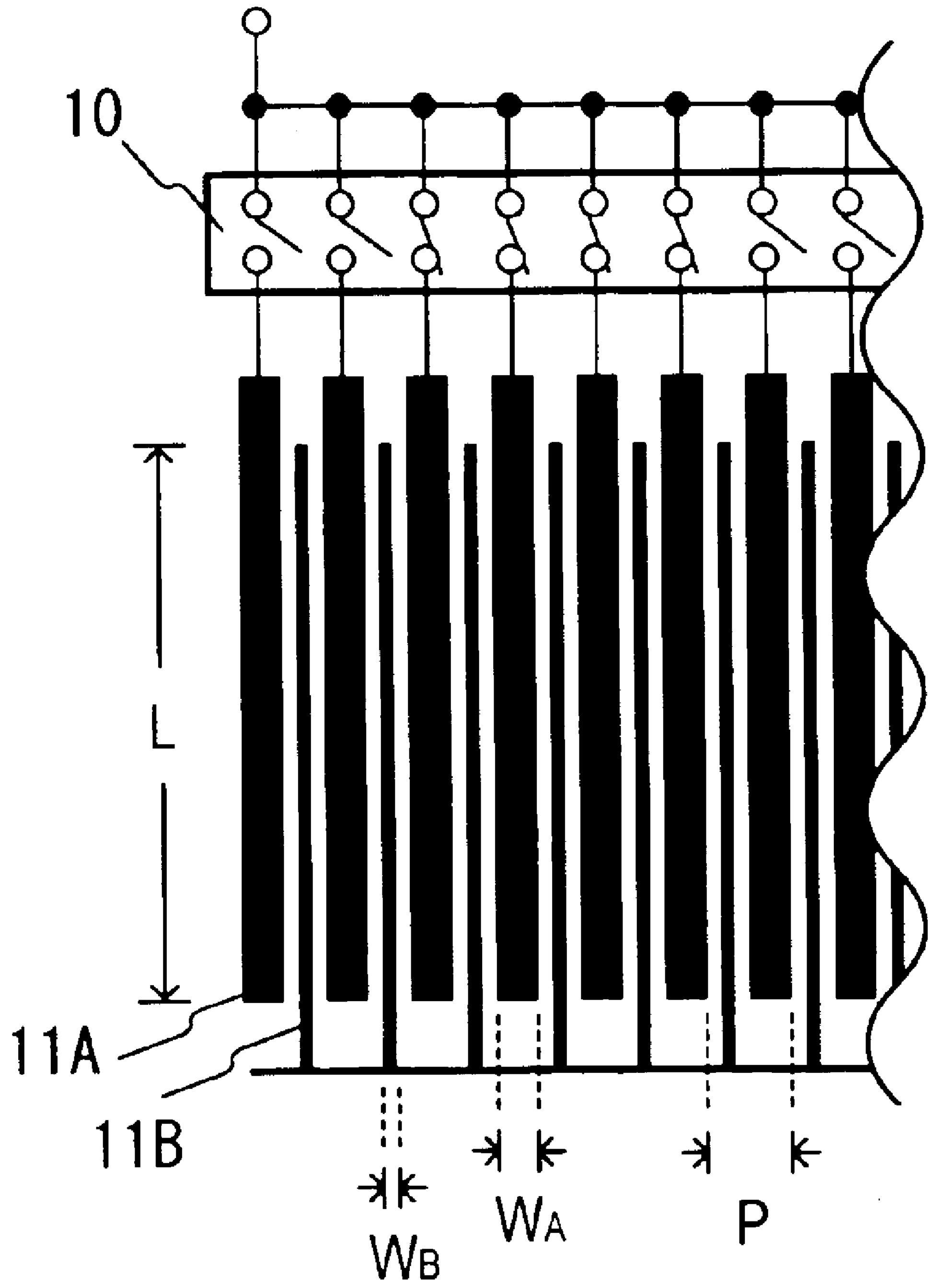
FIG. 5 shows a fragmentary top plan view of interdigital arrangement 11.

FIG. 5 shows a fragmentary top plan view of interdigital arrangement 11. Scanning system 10 is also shown in FIG. 5. Interdigital arrangement 11 has twenty electrode-finger pairs, a finger-overlap length (L) of 5 mm, and an interdigital periodicity (P) of 225 μm, which is the same as interdigital transducer 12. Comb-shaped electrode 11A has a finger width ($W_A$) of 45 μm, and comb-shaped electrode 11B has a finger width ($W_B$) of 12 μm. In the ultrasound radiation device in FIG. 4, scanning system 10 has twenty switches corresponding to the electrode-fingers of comb-shaped electrode 11A, respectively. The twenty switches form seventeen groups, of which each has four switches. In this way, one and the next of the groups have three common switches each other except the first switch of the one of the groups and the last switch of the next of the groups. For example, the second and the third of the groups have three common switches each other except the first switch of the second of the groups and the last switch of the third of the groups.

In the ultrasound radiation device in FIG. 4, if input electric signals are applied between counter electrode 3 and comb-shaped electrode 11A via the groups of scanning system 10 in turn, seventeen longitudinal waves are radiated into the material in turn. In this way, the seventeen longitudinal waves are radiated in the form of a scanned ultrasound beam as a whole into the material through silicone rubber 4. At the same time, Lamb waves are excited in piezoelectric substrate 1, and then, transmitted to interdigital transducer 12 along the parallel direction with the end surfaces of piezoelectric substrate 1. In this time, the use of glass plate 6 prevents the leakage of the Lamb wave into the material. Thus, the Lamb waves are detected at interdigital transducer 12 as delayed electric signals, which are amplified via amplifier 7 and supplied to comb-shaped electrode 11A as input electric signals again. Thus, supplying comb-shaped electrode 2A with the input electric signal via amplifier 7 causes a self-oscillation, and moreover causes the circuit construction simplified.

As mentioned above, the scanned ultrasound beam is radiated into the material. When the material is water, the ratio of the $V_W$ value to the V value is approximately 0.333, as mentioned above. On the other hand, the ratio of the interdigital periodicity (P) of interdigital arrangement 11 to the thickness (T) of piezoelectric substrate 1, that is 225/500, is 0.45, which is still smaller than four times the ratio of the $V_W$ value to the V value. Under such a condition of $P/T<4_W/V$, the grating lobes of each of the seventeen longitudinal waves are suppressed. Accordingly, the scanned ultrasound beam along the direction vertical to the lower end surface of piezoelectric substrate 1 is effectively radiated into water through silicone rubber 4.

Figure 6:
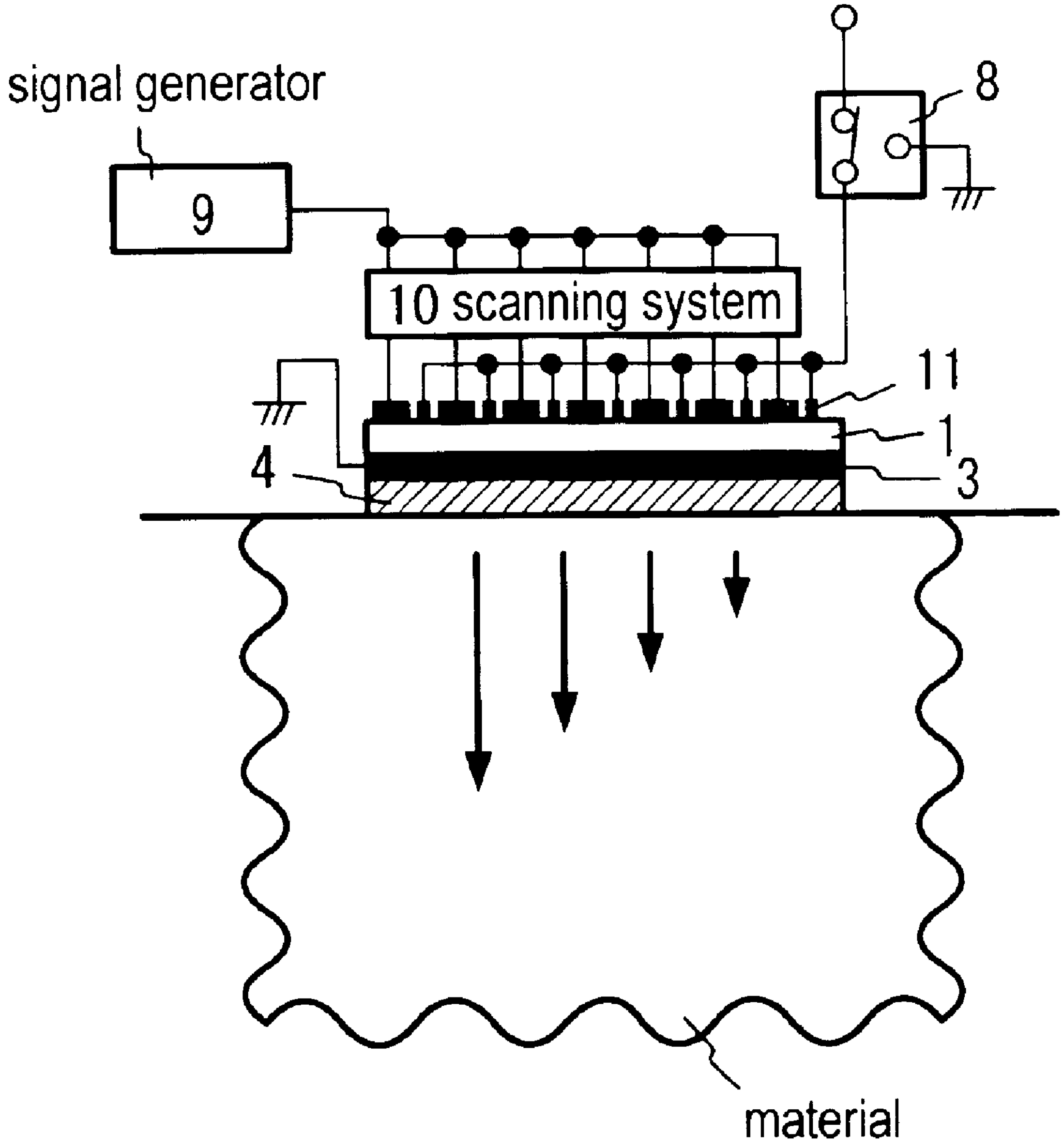
FIG. 6 shows a sectional view of an ultrasound radiation device according to a fourth embodiment of the present invention.

FIG. 6 shows a sectional view of an ultrasound radiation device according to a fourth embodiment of the present invention. The ultrasound radiation device comprises piezoelectric substrate 1, interdigital arrangement 2, counter electrode 3, silicone rubber 4, switch 8, signal generator 9, scanning system 10, and interdigital arrangement 11.

In the ultrasound radiation device in FIG. 6, if input electric signals from signal generator 9 are applied between counter electrode 3 and comb-shaped electrode 11A via the groups of scanning system 10 in turn, seventeen longitudinal waves are radiated into the material in turn. In this way, the seventeen longitudinal waves are radiated in the form of a scanned ultrasound beam as a whole into the material through silicone rubber 4.

Figure 7:
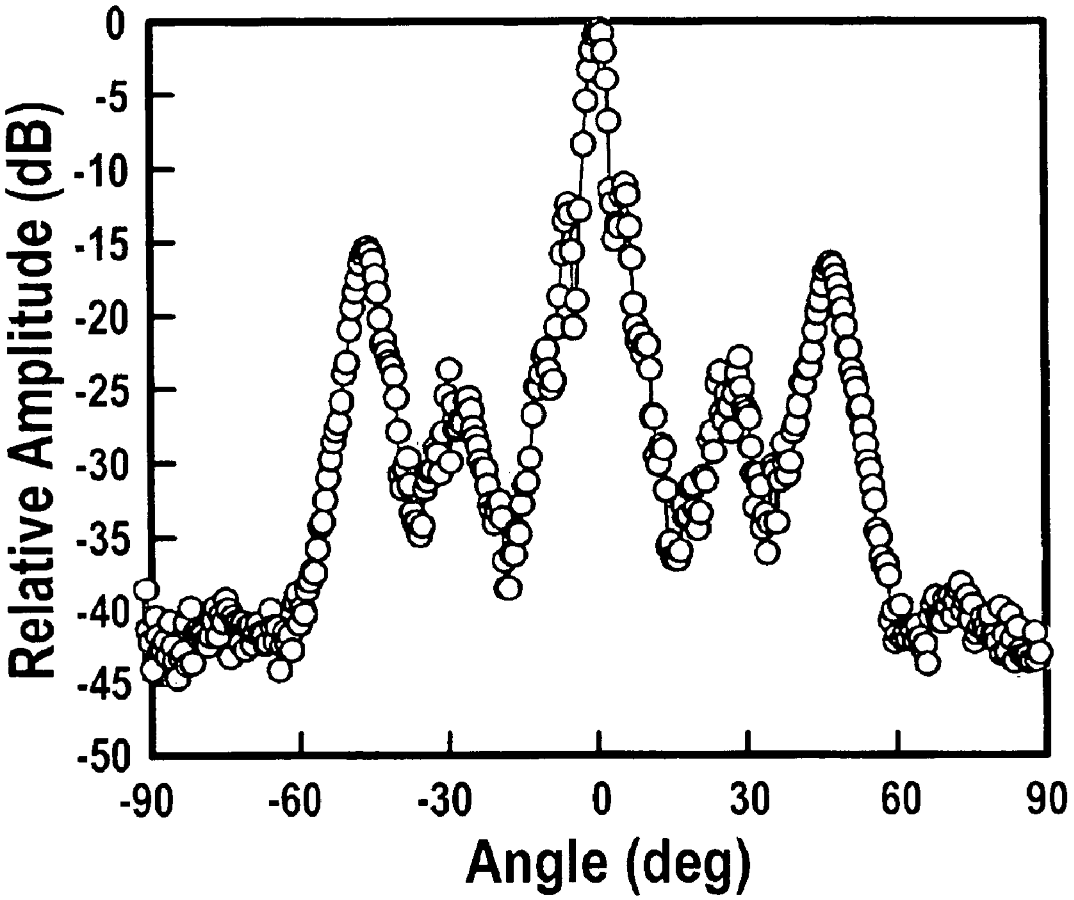
FIG. 7 shows a relationship between the relative amplitude and the radiation angle of the longitudinal wave into water from the ultrasound radiation device in FIG. 1.

FIG. 7 shows a relationship between the relative amplitude and the radiation angle of the longitudinal wave into water from the ultrasound radiation device in FIG. 1 in case that comb-shaped electrode 2B is electrically floated by switch 8. It should be noticed that there are grating lobes at −45° and 45° besides the main lobe. This means that the longitudinal wave composed of the main lobe and the grating lobes is effectively radiated into, for example, a cellular tissue through a skin, as well as water.

Figure 8:
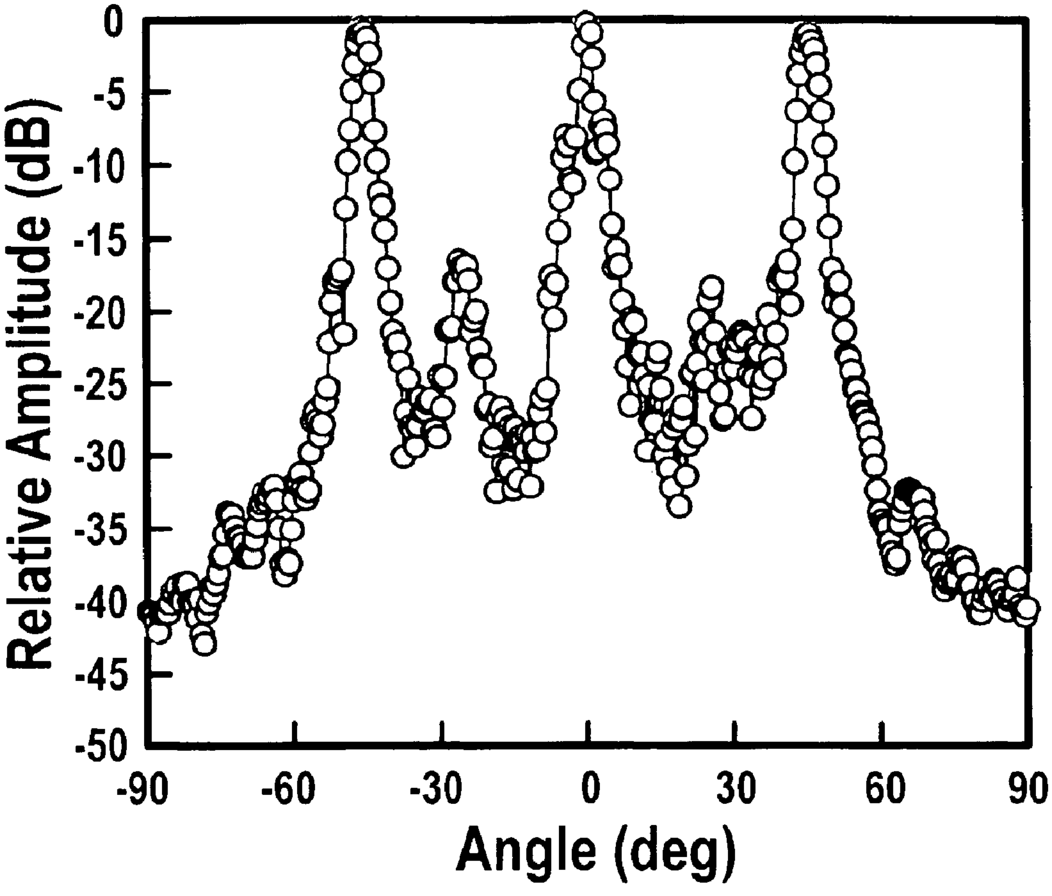
FIG. 8 shows a relationship between the relative amplitude and the radiation angle of the longitudinal wave into water from the ultrasound radiation device in FIG. 1.

FIG. 8 shows a relationship between the relative amplitude and the radiation angle of the longitudinal wave into water from the ultrasound radiation device in FIG. 1 in case that comb-shaped electrode 2B is electrically grounded by switch 8. In addition to the main lobe, there are grating lobes at −45° and 45° larger than those in FIG. 7. Thus, it is clear that the longitudinal wave composed of the main lobe and the grating lobes is effectively radiated into a material, and that the electrical condition of comb-shaped electrode 2B controls the existence of grating lobes.

Figure 9:
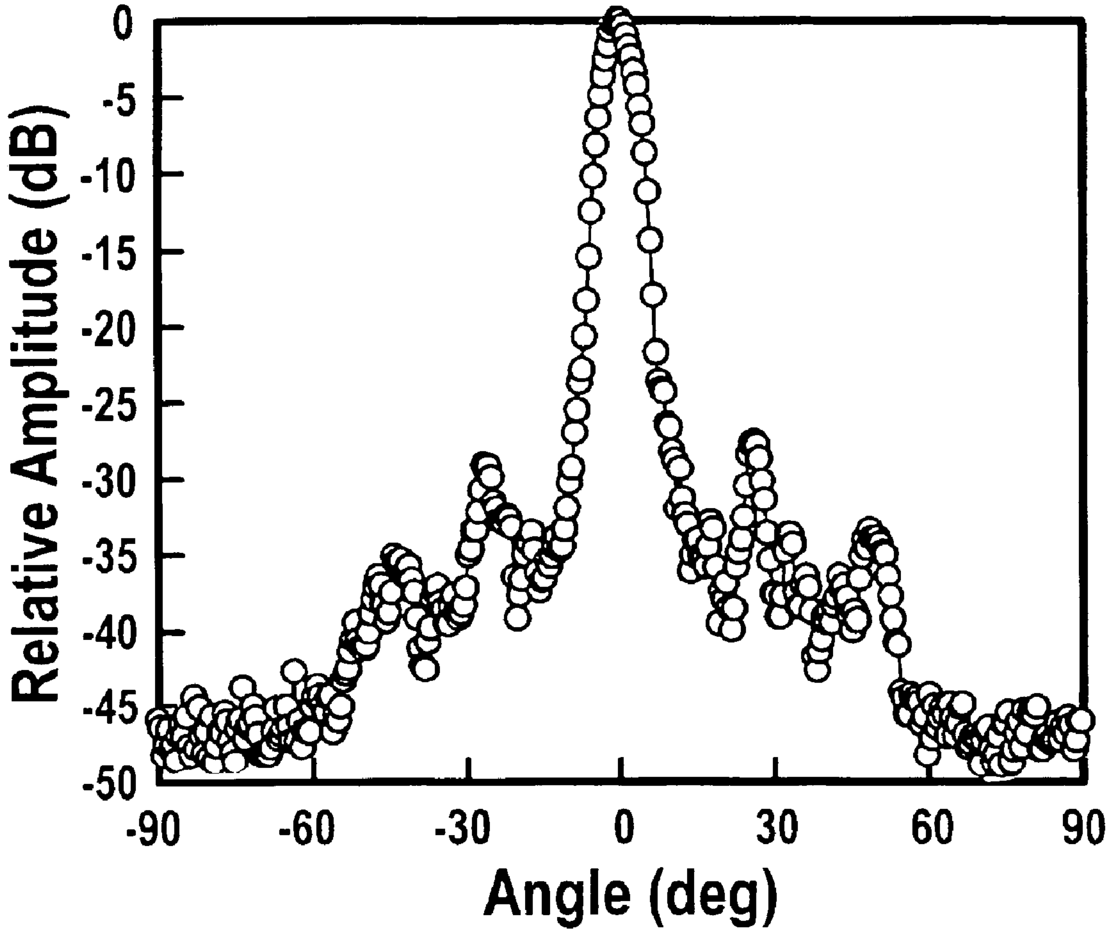
FIG. 9 shows a relationship between the relative amplitude and the radiation angle of one of the seventeen longitudinal waves into water from the ultrasound radiation device in FIG. 4.

FIG. 9 shows a relationship between the relative amplitude and the radiation angle of one of the seventeen longitudinal waves into water from the ultrasound radiation device in FIG. 4. It seems that there exists only the main lobe, because any grating lobe is suppressed. Thus, the use of interdigital arrangement 11 enables only a radiation vertical to the lower end surface of piezoelectric substrate 1 into water. As a result, the scanned ultrasound beam is effectively radiated into, for example, a cellular tissue through a skin, along a vertical direction to the lower end surface of piezoelectric substrate 1.

Figure 10:
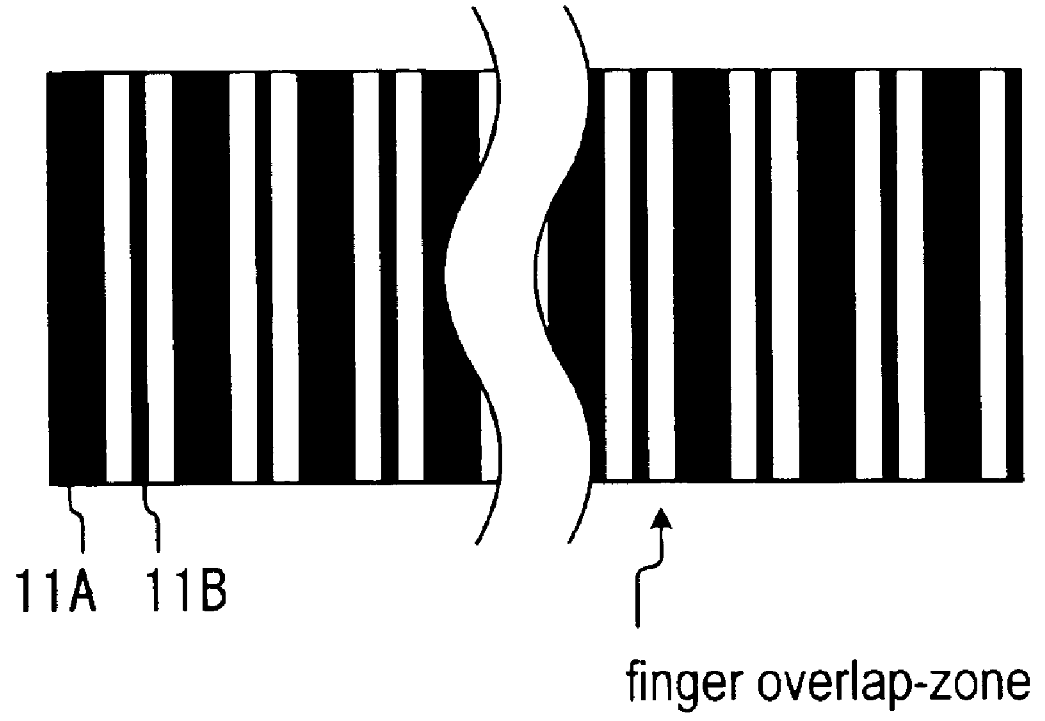
FIG. 10 shows a top plan view of the finger overlap-zone of interdigital arrangement 11.

FIG. 10 shows a top plan view of the finger overlap-zone of interdigital arrangement 11.

Figure 11:
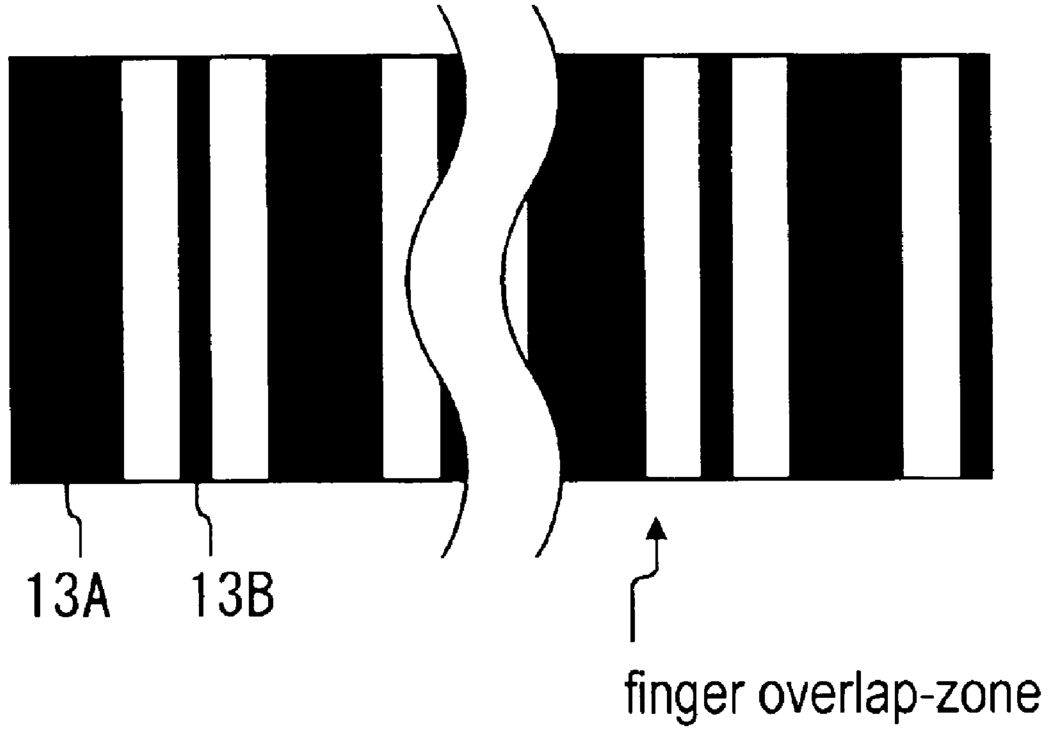
FIG. 11 shows a top plan view of the finger overlap-zone of interdigital arrangement 13.

FIG. 11 shows a top plan view of the finger overlap-zone of interdigital arrangement 13 of two comb-shaped electrodes (13A and 13B). Interdigital arrangement 13 has fifteen electrode-finger pairs, a finger-overlap length (L) of 5 mm, and an interdigital periodicity (P) of 300 μm. Comb-shaped electrode 13A has a finger width ($W_A$) of 60 μm, and comb-shaped electrode 13B has a finger width ($W_B$) of 15 μm. The finger overlap-zone of interdigital arrangement 13 and that of interdigital arrangement 11 are the same in size. In addition, the total amount of all the finger-areas of comb-shaped electrode 13A is the same as that of comb-shaped electrode 11A.

A comparison between FIGS. 10 and 11 indicates that interdigital arrangement 11 and interdigital arrangement 13 are different from each other with respect to the number of electrode-finger pairs, the finger widths ($W_A$ and $W_B$), and the interdigital periodicity (P). Actually, the number of electrode-pairs in interdigital arrangement 11 is 4/3 times that in interdigital arrangement 13. At the same time, the interdigital periodicity (P) of interdigital arrangement 11 is ¾ times that of interdigital arrangement 13, and the finger width ($W_A$) of interdigital arrangement 11 is also ¾ times that of interdigital arrangement 13. It is recognized that the use of interdigital arrangement 11 causes a sharper directionality of the longitudinal wave than interdigital arrangement 13. This means that increasing the number of electrode-finger pairs suppresses the grating lobes still more under a condition that the total amount of all the finger-areas of comb-shaped electrode used as an input electrode is constant. As a result, the number of electrode-finger pairs has influence on the directionality of the longitudinal wave into a material under the condition that the total amount of all the finger-areas of the comb-shaped electrode used as an input electrode is constant.

Figure 12:
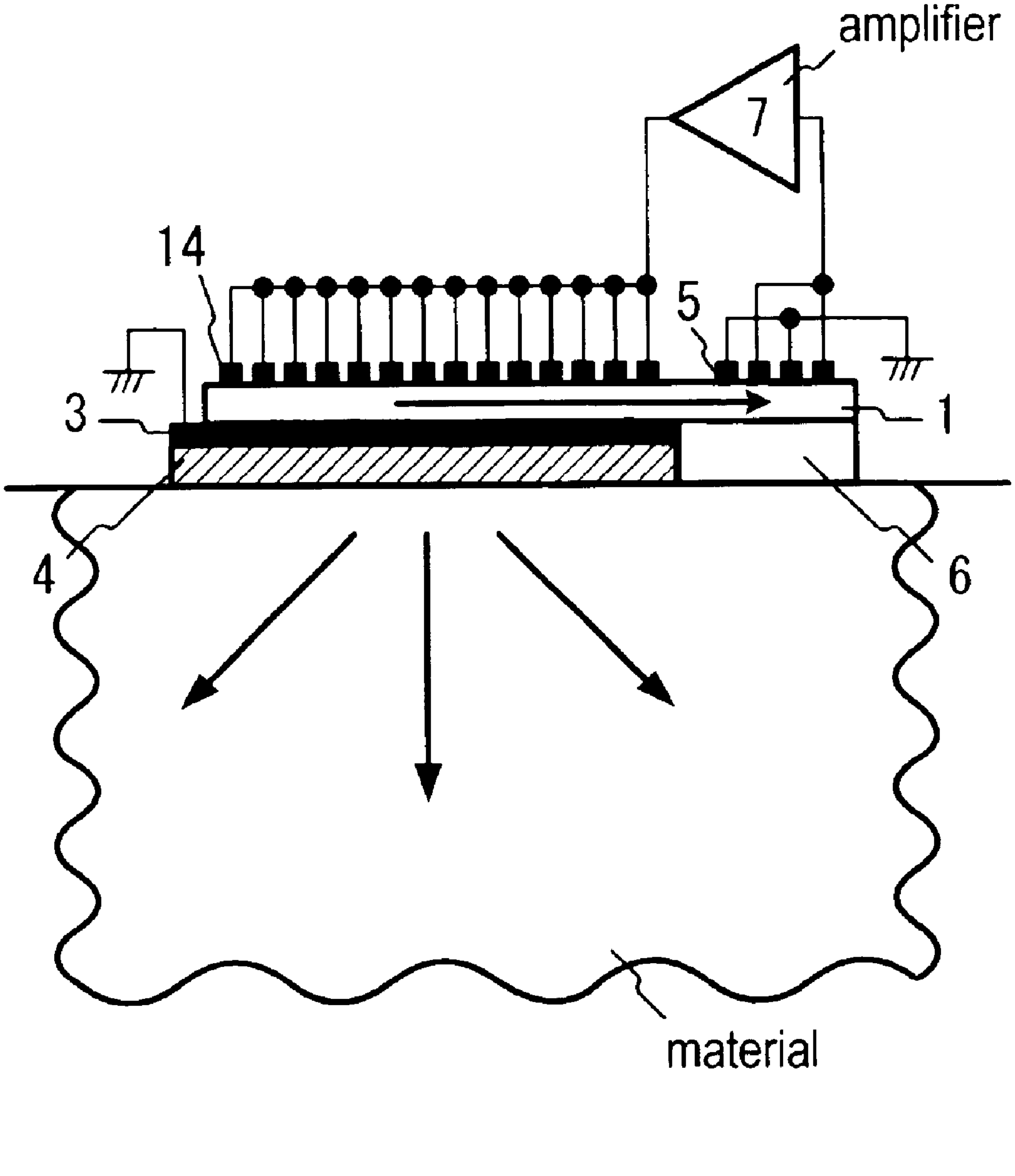
FIG. 12 shows a sectional view of an ultrasound radiation device according to a fifth embodiment of the present invention.

FIG. 12 shows a sectional view of an ultrasound radiation device according to a fifth embodiment of the present invention. The ultrasound radiation device comprises piezoelectric substrate 1, counter electrode 3, silicone rubber 4, interdigital transducer 5, glass plate 6, amplifier 7, and comb-shaped electrode 14.

Figure 13:
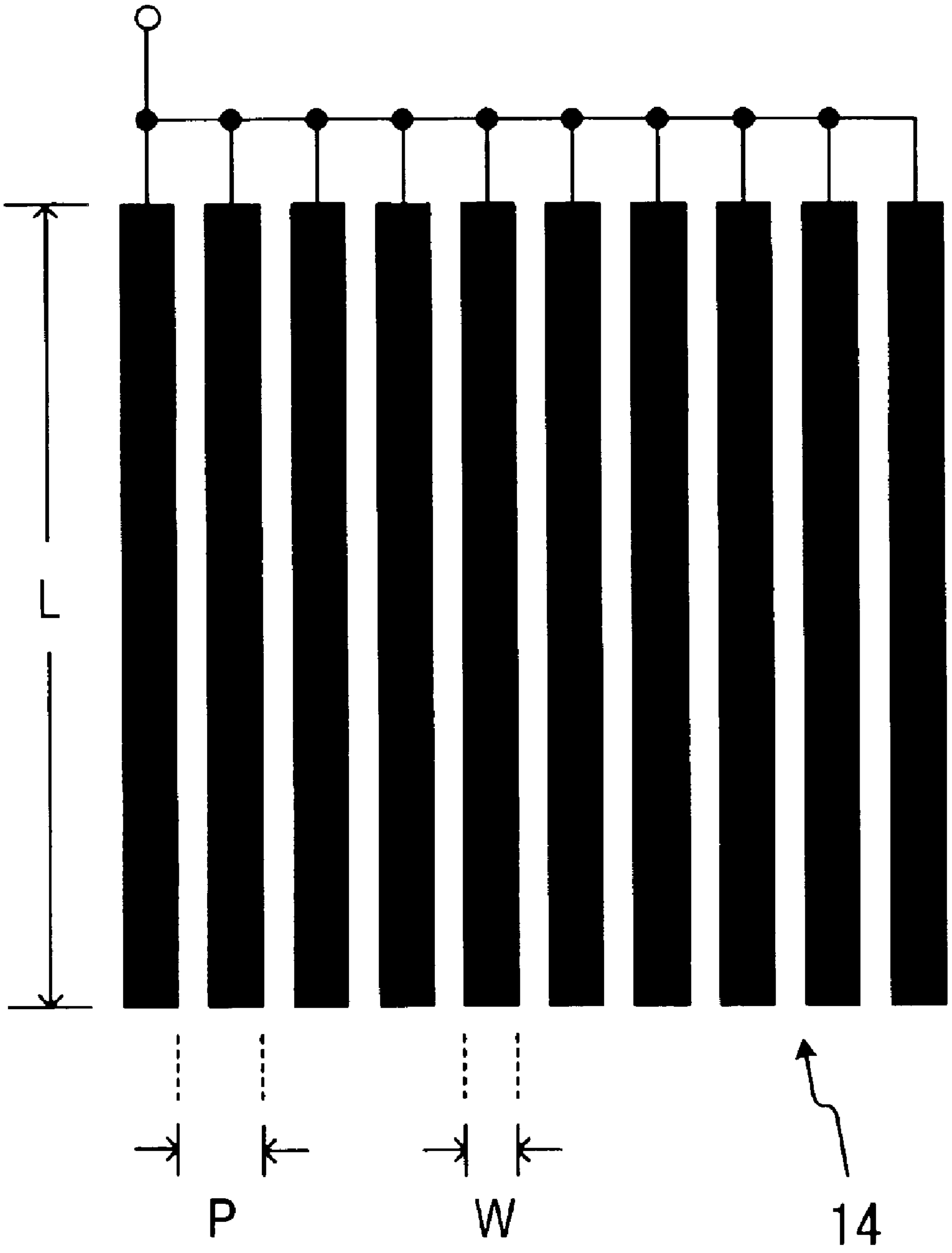
FIG. 13 shows a top plan view of comb-shaped electrode 14.

FIG. 13 shows a top plan view of comb-shaped electrode 14. Comb-shaped electrode 14 has twenty electrode-fingers, a finger-overlap length (L) of 5 mm, a finger width (W) of 700 μm, and an interdigital periodicity (P) of 900 μm, which is the same as interdigital transducer 5.

In the ultrasound radiation device in FIG. 12, if an electric signal is applied between counter electrode 3 and comb-shaped electrode 14, a longitudinal wave is radiated into a material through silicone rubber 4, as well as a Lamb wave is excited in piezoelectric substrate 1. When the material is water, the condition of $P/T \geqq 4V_W/V$ enables a multidirectional radiation of the longitudinal wave into water. In addition, comb-shaped electrode 14, interdigital transducer 5, and amplifier 7 form a self-oscillation type of delay-line oscillator.

Figure 14:
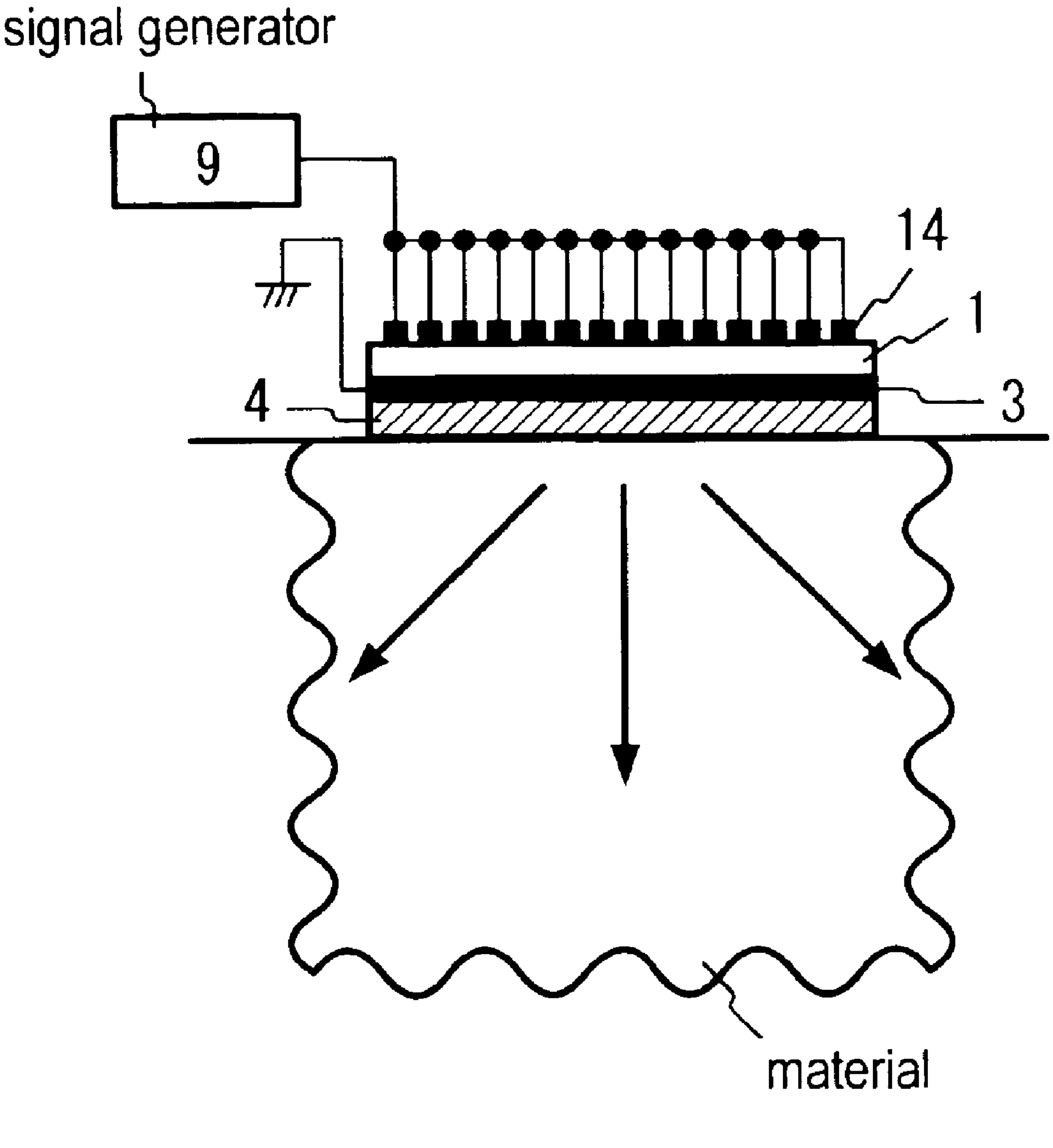
FIG. 14 shows a sectional view of an ultrasound radiation device according to a sixth embodiment of the present invention.

FIG. 14 shows a sectional view of an ultrasound radiation device according to a sixth embodiment of the present invention. The ultrasound radiation device comprises piezoelectric substrate 1, counter electrode 3, silicone rubber 4, signal generator 9, and comb-shaped electrode 14.

In the ultrasound radiation device in FIG. 14, if an electric signal from signal generator 9 is applied between counter electrode 3 and comb-shaped electrode 14, a longitudinal wave is radiated into a material through silicone rubber 4. When the material is water, the condition of $P/T \geqq 4V_W/V$ enables a multidirectional radiation of the longitudinal wave into water.

Figure 15:
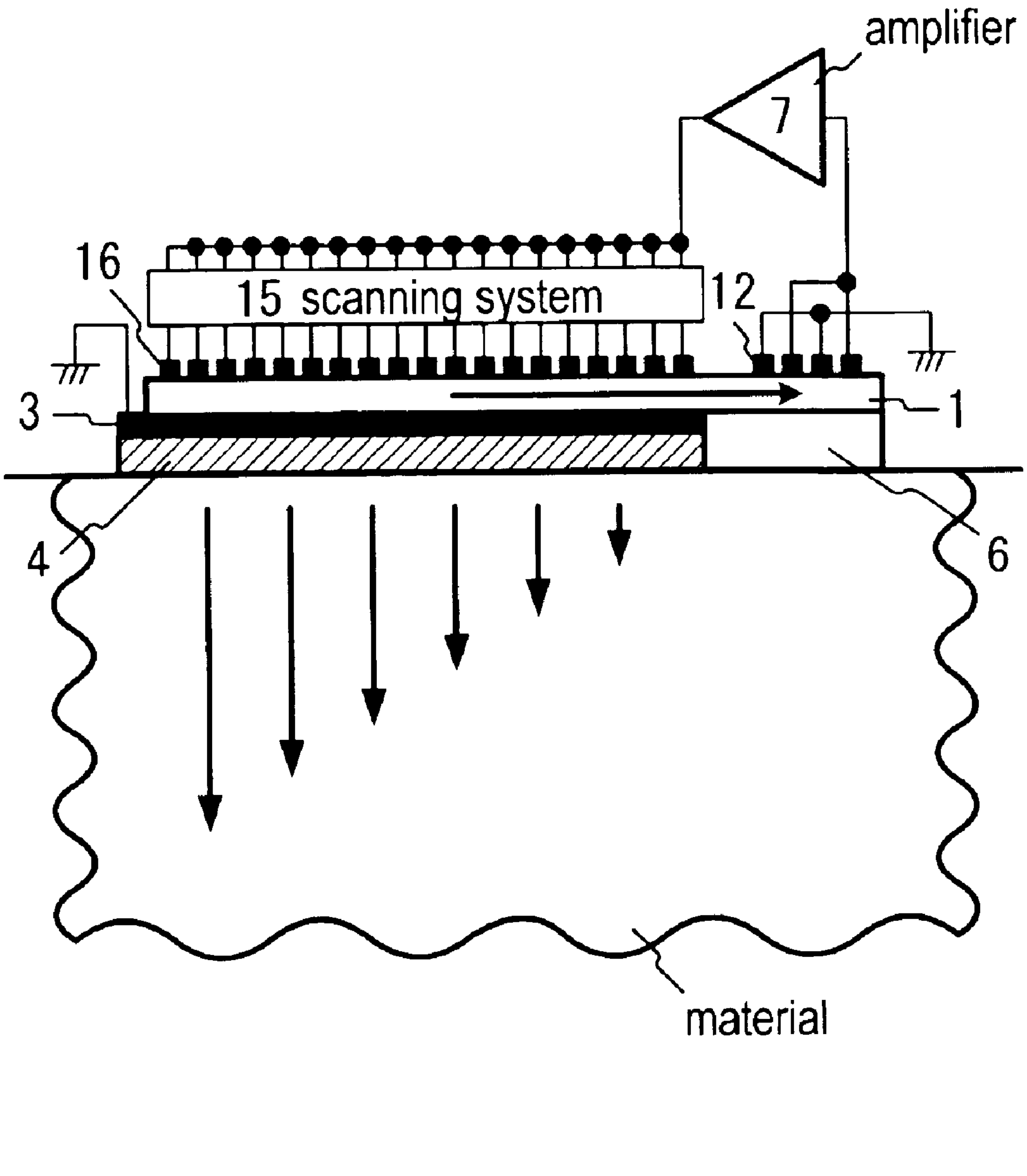
FIG. 15 shows a sectional view of an ultrasound radiation device according to a seventh embodiment of the present invention.

FIG. 15 shows a sectional view of an ultrasound radiation device according to a seventh embodiment of the present invention. The ultrasound radiation device comprises piezoelectric substrate 1, counter electrode 3, silicone rubber 4, glass plate 6, amplifier 7, interdigital transducer 12, scanning system 15, and comb-shaped electrode 16.

Figure 16:
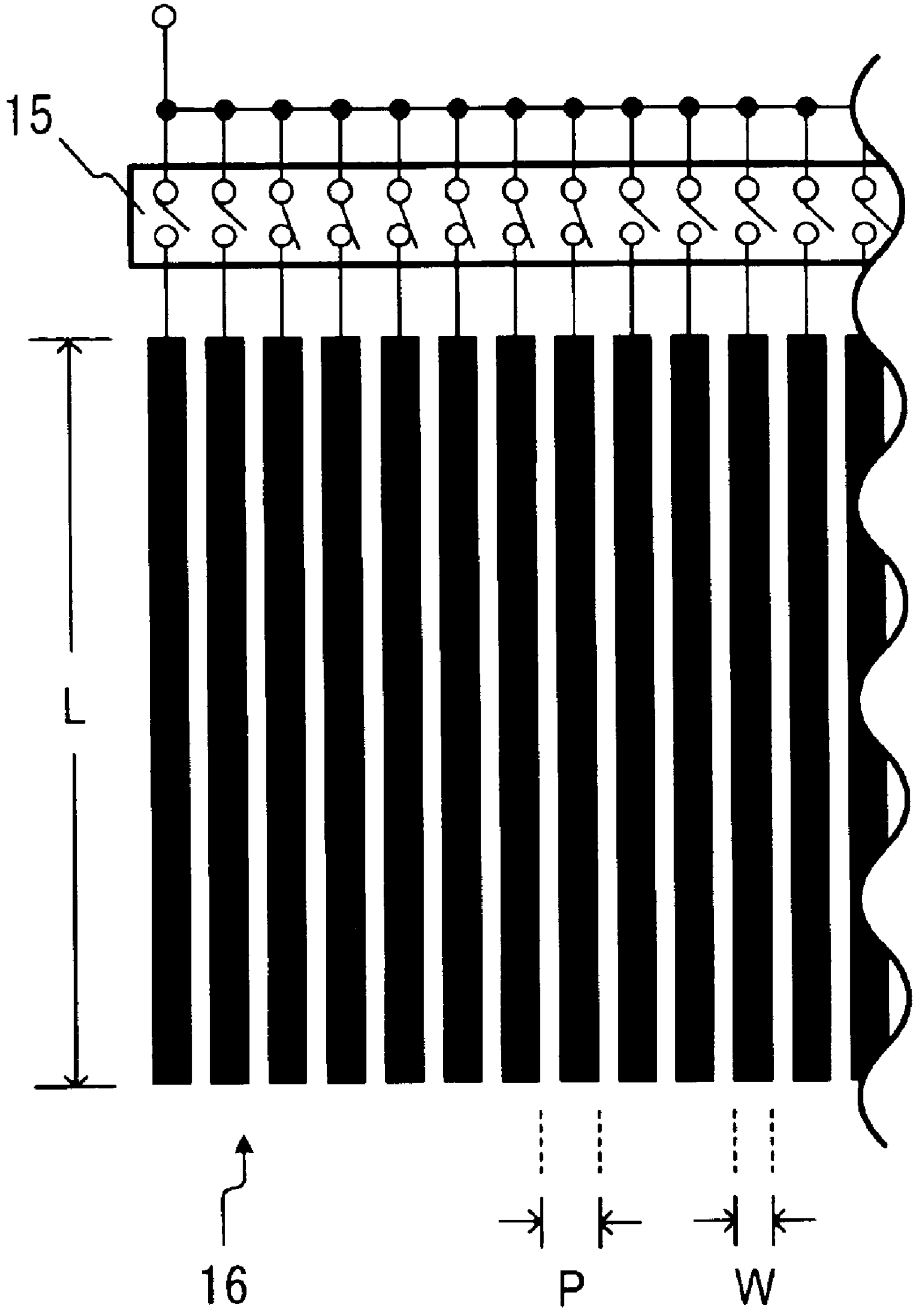
FIG. 16 shows a fragmentary top plan view of comb-shaped electrode 16 connected with scanning system 15.

FIG. 16 shows a fragmentary top plan view of comb-shaped electrode 16 connected with scanning system 15. Comb-shaped electrode 16 has forty electrode-fingers, a finger-overlap length (L) of 5 mm, a finger width (W) of 175 μm, and an interdigital periodicity (P) of 225 μm, which is the same as interdigital transducer 12. In the ultrasound radiation device in FIG. 15, scanning system 15 has forty switches corresponding to the electrode-fingers of comb-shaped electrode 16, respectively. The forty switches form thirty-five groups, of which each has six switches. In this way, one and the next of the groups have five common switches each other except the first switch of the one of the groups and the last switch of the next of the groups. For example, the third and the fourth of the groups have five common switches each other except the first switch of the third of the groups and the last switch of the fourth of the groups.

In the ultrasound radiation device in FIG. 15, if input electric signals are applied between counter electrode 3 and comb-shaped electrode 16 via the groups of scanning system 15 in turn, thirty-five longitudinal waves are radiated into a material in turn. In this way, the thirty-five longitudinal waves are radiated in the form of a scanned ultrasound beam as a whole into the material through silicone rubber 4. At the same time, a Lamb wave is excited in piezoelectric substrate 1. When the material is water, the condition of $P/T<4V_W/V$ enables a radiation of the scanned ultrasound beam along the direction vertical to the lower end surface of piezoelectric substrate 1 into water. In addition, comb-shaped electrode 16, interdigital transducer 12, and amplifier 7 form a self-oscillation type of delay-line oscillator.

Figure 17:
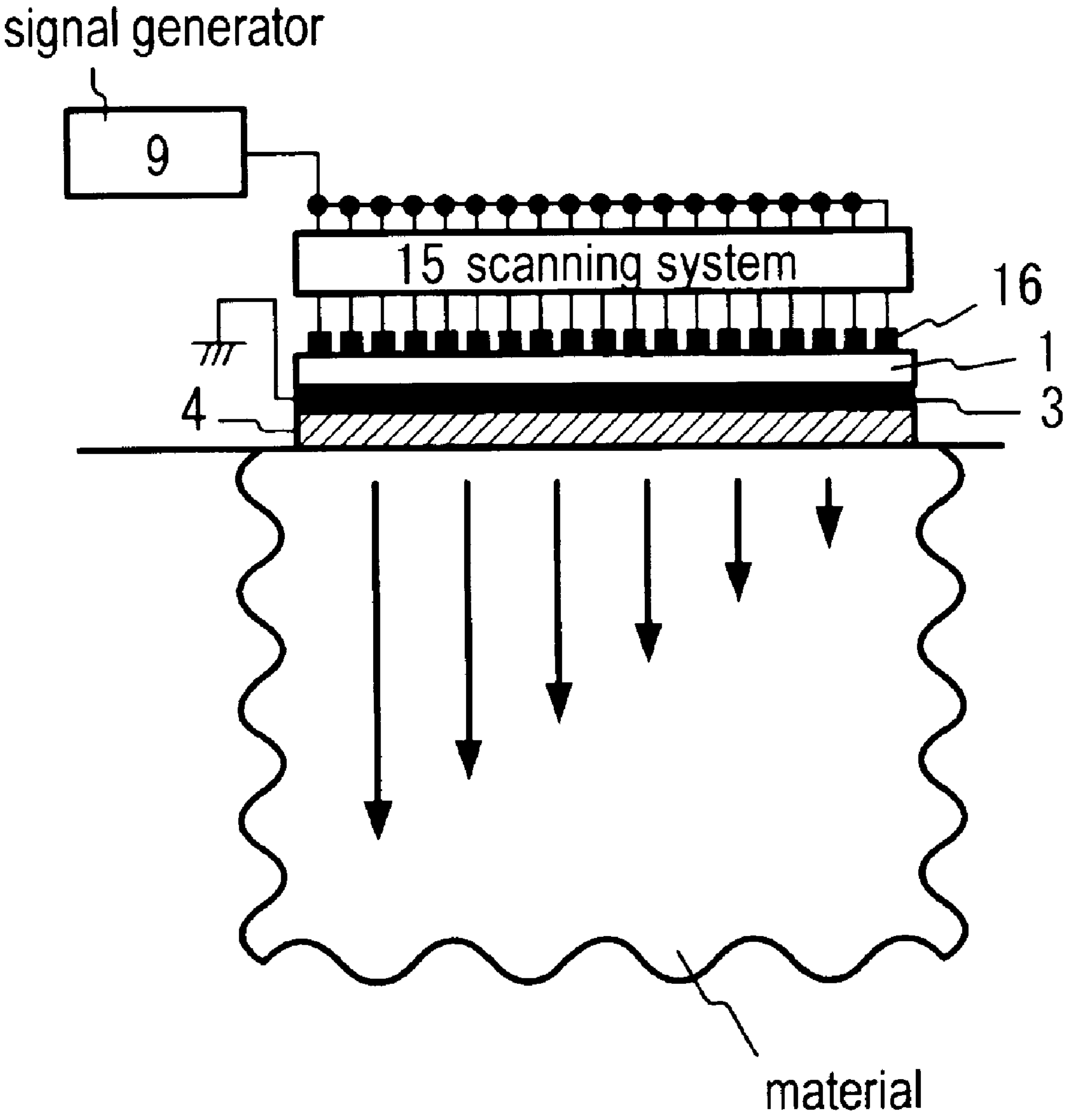
FIG. 17 shows a sectional view of an ultrasound radiation device according to an eighth embodiment of the present invention.

FIG. 17 shows a sectional view of an ultrasound radiation device according to an eighth embodiment of the present invention. The ultrasound radiation device comprises piezoelectric substrate 1, counter electrode 3, silicone rubber 4, signal generator 9, scanning system 15, and comb-shaped electrode 16.

In the ultrasound radiation device in FIG. 17, if input electric signals from signal generator 9 are applied between counter electrode 3 and comb-shaped electrode 16 via the groups of scanning system 15 in turn, thirty-five longitudinal waves are radiated into a material in turn. In this way, the thirty-five longitudinal waves are radiated in the form of a scanned ultrasound beam as a whole into the material through silicone rubber 4. When the material is water, the condition of $P/T<4V_W/V$ enables a radiation of the scanned ultrasound beam along the direction vertical to the lower end surface of piezoelectric substrate 1 into water.

While this invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims.

What is claimed is:

1. An ultrasound radiation device comprising:

a piezoelectric substrate having upper- and lower end surfaces;

an interdigital arrangement of two comb-shaped electrodes formed on said upper end surface of said piezoelectric substrate;

a counter electrode formed on said lower end surface of said piezoelectric substrate and in contact with a material through the lower end surface of said counter electrode;

an interdigital transducer formed on said upper end surface of said piezoelectric substrate; and an amplifier between one of said two comb-shaped electrodes and said interdigital transducer, said one of said two comb-shaped electrodes and said counter electrode receiving an electric signal, and radiating a longitudinal wave, composed of the main lobe and grating lobes, into said material, as well as exciting a Lamb wave in said piezoelectric substrate, said interdigital transducer detecting said Lamb wave as a delayed electric signal, said amplifier amplifying said delayed electric signal, and supplying said one of said two comb-shaped electrodes with an amplified electric signal as an input electric signal.

2. An ultrasound radiation device as defined in claim 1, wherein the finger width in said one of said two comb-shaped electrodes is wider than that in the other of said two comb-shaped electrodes.

3. An ultrasound radiation device as defined in claim 1, wherein increasing the number of electrode-finger pairs in said interdigital arrangement suppresses said grating lobes under a condition that the total amount of all the finger-areas of said one of said two comb-shaped electrodes is constant.

4. An ultrasound radiation device as defined in claim 1, wherein making the ratio of the interdigital periodicity of said interdigital arrangement to the thickness of said piezoelectric substrate smaller than four times the ratio of the longitudinal wave velocity in said material to the longitudinal wave velocity in said piezoelectric substrate suppresses said grating lobes.

5. An ultrasound radiation device as defined in claim 1, wherein said piezoelectric substrate is made of a piezoelectric ceramic plate, the polarization axis thereof being parallel to the thickness direction thereof.

6. An ultrasound radiation device as defined in claim 1, wherein said material is a liquid matter.

7. An ultrasound radiation device as defined in claim 1, wherein said material is a cellular tissue.

8. An ultrasound radiation device as defined in claim 1 further comprising a polymer film, with which said lower end surface of said counter electrode is coated.

9. An ultrasound radiation device as defined in claim 1 further comprising a nonpiezoelectric plate formed on said lower end surface of said piezoelectric substrate.

10. An ultrasound radiation device as defined in claim 1, wherein said material is a cellular tissue having an ointment thereon through a skin.

11. An ultrasound radiation device as defined in claim 1 further comprising:

a scanning system composed of groups of switches corresponding to the electrode-fingers of said one of said two comb-shaped electrodes, respectively, one and the next of said groups having common switches each other except the first switch of said one of said groups and the last switch of said next of said groups, said one of said two comb-shaped electrodes, together with said counter electrode, receiving input electric signals via said groups in turn, and radiating longitudinal waves into said material in the form of a scanned ultrasound beam as a whole.

12. An ultrasound radiation device comprising:

a piezoelectric substrate having upper- and lower end surfaces;

a comb-shaped electrode formed on said upper end surface of said piezoelectric substrate; and a counter electrode formed on said lower end surface of said piezoelectric substrate and in contact with a material through the lower end surface of said counter electrode, an interdigital transducer formed on said upper end surface of said piezoelectric substrate; and an amplifier between said comb-shaped electrode and said interdigital transducer, said comb-shaped electrode and said counter electrode receiving an electric signal, and radiating a longitudinal wave, composed of the main lobe and grating lobes, into said material, as well as exciting a Lamb wave in said piezoelectric substrate, said interdigital transducer detecting said Lamb wave as a delayed electric signal, said amplifier amplifying said delayed electric signal, and supplying said comb-shaped electrode with an amplified electric signal as an input electric signal.

13. An ultrasound radiation device as defined in claim 12, wherein increasing the number of electrode-fingers in said comb-shaped electrode suppresses said grating lobes under a condition that the total amount of all the finger-areas of said comb-shaped electrode is constant.

14. An ultrasound radiation device as defined in claim 12, wherein making the ratio of the interdigital periodicity of said comb-shaped electrode to the thickness of said piezoelectric substrate smaller than four times the ratio of the longitudinal wave velocity in said material to the longitudinal wave velocity in said piezoelectric substrate suppresses said grating lobes.

15. An ultrasound radiation device as defined in claim 12, wherein said material is a liquid matter.

16. An ultrasound radiation device as defined in claim 12, wherein said material is a cellular tissue.

17. An ultrasound radiation device as defined in claim 12 further comprising a polymer film, with which said lower end surface of said counter electrode is coated.

18. An ultrasound radiation device as defined in claim 12 further comprising a nonpiezoelectric plate formed on said lower end surface of said piezoelectric substrate.

19. An ultrasound radiation device as defined in claim 12, wherein said material is a cellular tissue having an ointment thereon through a skin.

20. An ultrasound radiation device as defined in claim 12 further comprising:

a scanning system composed of groups of switches corresponding to the electrode-fingers of said comb-shaped electrode, respectively, one and the next of said groups having common switches each other except the first switch of said one of said groups and the last switch of said next of said groups, said comb-shaped electrode and said counter electrode receiving input electric signals via said groups in turn, and radiating longitudinal waves into said material in the form of a scanned ultrasound beam as a whole.

* * * * *